(12) United States Patent
Davodian

(10) Patent No.: US 8,821,574 B2
(45) Date of Patent: Sep. 2, 2014

(54) VALVE ASSEMBLIES FOR EXPANDABLE IMPLANTS AND TISSUE EXPANDERS

(71) Applicant: Amir Davodian, Amersfoort (NL)

(72) Inventor: Amir Davodian, Amersfoort (NL)

(73) Assignee: Mentor Worldwide LLC, Santa Barbara, CA (US)

( * ) Notice: Subject to any disclaimer, the term of this patent is extended or adjusted under 35 U.S.C. 154(b) by 0 days.

(21) Appl. No.: 13/705,349

(22) Filed: Dec. 5, 2012

(65) Prior Publication Data
US 2014/0156001 A1    Jun. 5, 2014

(51) Int. Cl.
*A61F 2/12*    (2006.01)

(52) U.S. Cl.
CPC .......................... *A61F 2/12* (2013.01)
USPC ............................................................ 623/8

(58) Field of Classification Search
USPC ............................................ 623/7–8; 450/38
See application file for complete search history.

(56) References Cited

U.S. PATENT DOCUMENTS

| | | | |
|---|---|---|---|
| 3,020,260 A | 2/1962 | Nelson | |
| 3,293,663 A | 12/1966 | Cronin | |
| 3,600,718 A | 8/1971 | Boone | |
| 3,883,902 A | 5/1975 | Lynch | |
| 3,919,724 A | 11/1975 | Sanders et al. | |
| 4,263,682 A | 4/1981 | Bejarano | |
| 4,662,883 A | 5/1987 | Bell et al. | |
| 4,775,379 A * | 10/1988 | Fogarty et al. | 623/8 |
| 4,930,535 A | 6/1990 | Rinehold | |
| 4,944,749 A | 7/1990 | Becker | |
| 5,019,101 A * | 5/1991 | Purkait et al. | 623/8 |
| 5,127,627 A * | 7/1992 | Wiser | 251/149.1 |
| 5,456,716 A | 10/1995 | Iversen et al. | |
| 5,507,808 A | 4/1996 | Becker | |
| 6,752,965 B2 | 6/2004 | Levy | |

FOREIGN PATENT DOCUMENTS

EP         0400628 A1    12/1990

\* cited by examiner

*Primary Examiner* — Suzette J Gherbi

(57) ABSTRACT

A valve assembly for an implant has an inner shell, a self-sealing material disposed within the inner shell, and an insertion pathway extending through the self-sealing material. At least one gap is formed in the self-sealing material that intersects with the insertion pathway to define a proximal pathway section and a distal pathway section. A filling tube is passed through the valve assembly for filling the outer shell of the implant with a fluid. After the implant is filled, the filling tube is removed. As the filling tube is removed, if the self-sealing material within the distal section of the pathway is unable to self-seal before the fluid reaches its proximal end, the fluid is diverted into the gap. The time that elapses before the gap is completely filled by the fluid provides sufficient time for the self-sealing material within the proximal section of the pathway to self-seal.

22 Claims, 5 Drawing Sheets

VALVE ASSEMBLIES FOR EXPANDABLE IMPLANTS AND TISSUE EXPANDERS

BACKGROUND OF THE INVENTION

1. Field of the Invention

The present invention generally relates to medical devices, and more specifically relates to valve assemblies for implantable prostheses and tissue expanders.

2. Description of the Related Art

Implantable prostheses are commonly used to replace or augment body tissue. In instances of breast cancer, it may be necessary to remove some or all of the mammary gland and surrounding tissue. This surgery leaves a void that can be filled with an implantable prosthesis that supports surrounding tissue and provides a normal body appearance, eliminating much of the shock and depression that often follows breast cancer surgeries. Implantable prostheses may also used for breast augmentation procedures.

Tissue expanders are implantable devices that are placed beneath the skin and then gradually inflated to stretch the overlying tissue. Tissue expanders are commonly used to create a pocket for receiving a permanent prosthesis or to generate an increased skin surface area in anticipation of utilizing the newly grown skin for grafting or reconstruction procedures. After implantation, a solution, such as a saline solution, is periodically injected into the tissue expander to increase the volume of the tissue expander. Between injections, the surrounding skin is permitted to stretch and grow to create the increased skin surface. The solution may also be withdrawn from the tissue expander to reduce the internal volume and size of the expander.

Implantable prostheses and tissue expanders typically have a silicone shell that is manufactured by dipping an appropriately sized and shaped mandrel into a biocompatible silicone elastomer. Once the silicone shell has been formed, it is removed from the mandrel. The dip-molding process results in the formation of a silicone shell having a mandrel opening, e.g., a circular hole, in one of its faces. The mandrel opening is subsequently covered with a patch that seals the mandrel opening to form a fluid impervious implant shell. The patch may be attached to the implant shell using silicone rubber or other similar biocompatible adhesives. The completed shell can remain unfilled, be pre-filled, or intraoperatively filled through a small fill port or valve with a solution, such as saline solution, gel, foam, or combinations of these materials.

In many instances, implantable prostheses and tissue expanders have valves that allow medical personnel to add and remove fluid for adjusting the size of the devices. The valves used in these implants tend to be large and palpable. Permanent implants, e.g., breast implants, have filling tubes which may be used to add and withdraw fluid, however, these implants typically do not allow for adjustment of the implant after the filling tube is removed. As such, the pathway left after withdrawal of the filling tube is permanently closed.

There have been many efforts directed to providing valves for implants. U.S. Pat. No. 4,263,682 discloses a self-sealing valve for a fluid fillable implant, such as a mammary prosthesis, having first and second planar members that are bonded together in such a manner that leaves a bonded region and an elongated, unbonded region therebetween. Openings are formed in the planar members of the valve to provide for communication between the unbonded region and the inside and outside of the valve. The openings are offset from one another so that the openings in the unbonded region form a normally open channel through the valve. At least one of the planar members is sufficiently flexible to close the normally open channel in response to fluid pressure from within a fluid filled implant. Unfortunately, in use, it has been observed that the interior fluid pressure is not sufficient to prevent the leakage of fluid through the valve.

U.S. Pat. No. 3,600,718 to Boone discloses an inflatable prosthesis having an inflatable shell and a filling stem for introducing a filling fluid to inflate the shell. At the point of introduction of the filling stem, there is provided a capsule of sealing gel through which the stem passes. After implantation and inflation, the stem is withdrawn, either wholly or partially, and the gel in the capsule seals the stem outlet against leakage from the inflating fluid.

U.S. Pat. No. 5,019,101 to Purkait et al. discloses an implantable device having a self-sealing valve including a main body portion having a channel for receiving a fill tube. The valve includes a gel-filled chamber in which the main body portion thereof is disposed. The main body portion has a free end that is occluded by the gel once the fill tube has been withdrawn from the fill tube chamber.

In spite of the above advances, there remains a need for prosthetic implants and tissue expanders having valve assemblies that are highly leak resistant and that facilitate adding and removing solution from the implant shell. There also remains a need for prosthetic implants and tissue expanders having valve assemblies that enable solution to be easily added and removed both before and after implantation. In addition, there remains a need for implants and tissue expanders having valve assemblies having a low profile, and that are minimally palpable.

SUMMARY OF THE INVENTION

In one embodiment, a valve assembly for an expandable implant includes an inner shell having an inlet and an outlet, a self-sealing material disposed within the inner shell, and an insertion pathway for a filling tube extending through the self-sealing material, whereby the insertion pathway extends from the inlet to the outlet of the inner shell. In one embodiment, the seal-sealing material is a silicone material, such as a liquid silicone rubber. In one embodiment, the self-sealing material may be liquid silicone rubber material sold by APPLIED Silicone, part number 40029. In one embodiment, the liquid silicone rubber has a Shore A hardness rating of 30.

In one embodiment, at least one gap is formed in the self-sealing material. The at least one gap intersects the filling tube insertion pathway to define a proximal section of the insertion pathway and a distal section of the insertion pathway. The at least one gap formed in the self-sealing material preferably spaces and divides the proximal and distal sections of the insertion pathway from one another.

In one embodiment, more than one gap may be formed in the self-sealing material along the filling tube insertion path of the valve assembly. Each of the gaps may be formed by making a knife cut that intersects and passes through the insertion path. In one embodiment, the gaps "cut" or formed in the self-sealing material have a larger cross-section than the cross-section of the insertion pathway.

In one embodiment, the outlet of the inner shell desirably includes an outlet opening passing through the wall of the inner shell. In one embodiment, the outlet opening has a cylindrical or circular shape. The outlet opening may include a chamber, cartridge, ring or tube that maintains the shape of the outlet opening and that is adapted to receive and seat the distal end of a filling tube, as will be described in more detail herein.

In one embodiment, the insertion pathway extends along a straight line between the inlet and the outlet of the inner shell.

In one embodiment, the insertion pathway extends diagonally through the self-sealing material disposed within the inner shell. The inlet of the insertion pathway is preferably accessible outside the implant shell and the outlet of the insertion pathway is preferably in fluid communication with the internal chamber of the implant shell.

In one embodiment, the expandable implant has an outer shell with an outer surface, an inner surface, and an outer shell opening (e.g., a mandrel opening) extending from the outer surface to the inner surface. In one embodiment, the valve assembly covers the outer shell opening for closing and sealing the outer shell opening.

In one embodiment, a filling tube is used for filling the implant. In one embodiment, upon insertion, the filling tube passes through the inlet of the inner shell of the valve assembly, extends through the self-sealing material within the inner shell for opening a pathway through the self-sealing material, and has a distal end coupled with the outlet chamber at the outlet of the inner shell for filling the outer shell of the implant with a solution, such as a saline solution, a silicone gel, foam, or combinations thereof.

In one embodiment, the outer shell of the implant contains a solution having less viscosity than the self-sealing material disposed within the inner shell of the valve assembly. In one embodiment, the self-sealing material is a liquid silicone rubber and the solution within the outer shell of the implant is a saline solution, a silicone gel, foam, or combination thereof.

In one embodiment, the valve assembly includes a biocompatible patch and the inner shell is secured to the biocompatible patch. In one embodiment, the expandable implant has an outer shell with an outer shell opening and the patch closes the outer shell opening for sealing the expandable implant. When the patch is secured over the outer shell opening, the inner shell of the valve assembly is located inside the outer shell.

In one embodiment, the gap is formed during a casting process by using a mold having a rib. In one embodiment, the gap is molded into the patch that is secured to the inner shell after the molding of the patch with the gap is completed. The gap may also be molded into the self-sealing material. In one embodiment, two or more gaps may be formed. After the filling tube is removed from the valve assembly, the gap divides the insertion path into two sections, namely the proximal section and the distal section that are divided from one another and that are spaced from one another by the gap. The gap preferably diverts fluid from reaching the proximal section of the insertion pathway so that the silicone rubber has time to seal to prevent leakage. The proximal section of the insertion pathway is preferably used as a back-up for the distal section of the insertion pathway. If the distal section fails to seal, the proximal section serves as the back-up to prevent leakage, as well.

In one embodiment, an expandable implant includes an outer shell having an outer surface, an inner surface, and an outer shell opening extending from the outer surface to the inner surface. A valve assembly preferably closes the outer shell opening and is used for selectively inserting fluid into or withdrawing fluid from the implant. In one embodiment, the valve assembly desirably has an inner shell having an inlet and an outlet, a self-sealing material disposed within the inner shell, an insertion pathway extending through the self-sealing material, whereby the insertion pathway extends from the inlet to the outlet of the inner shell, and at least one gap formed in the self-sealing material and intersecting with the insertion pathway extending through the self-sealing material to define a proximal section of the insertion pathway and a distal section of the insertion pathway. The at least one gap formed in the self-sealing material spaces and divides the proximal and distal sections of the insertion pathway from one another.

In one embodiment, a filling tube preferably extends through the valve assembly from outside the outer shell to inside the outer shell for opening the valve assembly for inflating and deflating the implant using a solution, such as a saline solution. In one embodiment, the filling tube, when advanced through the valve assembly, passes through the inlet of the inner shell, extends along the insertion pathway through the self-sealing material for forming an opening in the self-sealing material, and is in communication with the outlet of the inner shell.

In one embodiment, the outlet of the inner shell comprises an outlet opening passing through the wall of the inner shell. The outlet opening is desirably in fluid communication with an internal chamber of the outer shell of an expandable implant or tissue expander. The outlet opening may have a cylindrical or circular shape.

In one embodiment, the inner shell containing the self-sealing material has a diameter of 13 mm and a height of 3 mm. In another embodiment, the inner shell containing the self-sealing material has a diameter of 38 mm and height of 4 mm. In one embodiment, the inner shell containing the self-sealing material has a diameter of at least 9 mm.

In one embodiment, an outlet chamber, ring, cartridge, or tube is provided at the outlet of the inner shell for receiving a distal end of the filling tube to protect the filling tube and maintain the shape and configuration of the wall of the inner shell. In one embodiment, the receiving chamber has a cylindrical or tubular shape.

In one embodiment, a relatively long filing tube or needle is used to selectively add and remove fluid from an expandable implant. In one embodiment, the filling tube is inserted diagonally through a valve assembly that contains a self-sealing material such as silicone rubber. The inserted filling tube opens a pathway through the silicone rubber material within the inner shell of the valve assembly. The pathway through the self-sealing material closes as the filling tube is removed from the valve assembly due to the very high elastic properties of the silicone rubber, which provides self-sealing characteristics. In one embodiment, the force required to remove the filling tube from the valve assembly is about 5-15 Newtons and more preferably about 9 Newtons.

In one embodiment, in order to minimize the likelihood of fluid leakage as the filling tube is removed from the valve assembly, a small volumetric space, gap and/or groove is created in the middle of the insertion pathway for the filling tube. The gap divides the insertion pathway into a proximal section and a distal section. After filling the implant and while withdrawing the filling tube from the valve assembly, if the distal section of the insertion pathway is unable to seal itself before any back pressure from within the implant causes fluid to pass completely through the distal section, the fluid that escapes from the distal section will be diverted into the at least one gap formed in the self-sealing material. The time that elapses as the escaping fluid or solution fills the gap provides time for the proximal section of the insertion pathway to seal. In one embodiment, the volume and dimensions of the gap may be modified to compliment the specific properties of the self-sealing silicone material used. In one embodiment, providing at least one gap enables the overall length of an insertion pathway to be shorter than otherwise possible.

These and other preferred embodiments of the present invention will be described in more detail below.

DETAILED DESCRIPTION

Figure 1A:
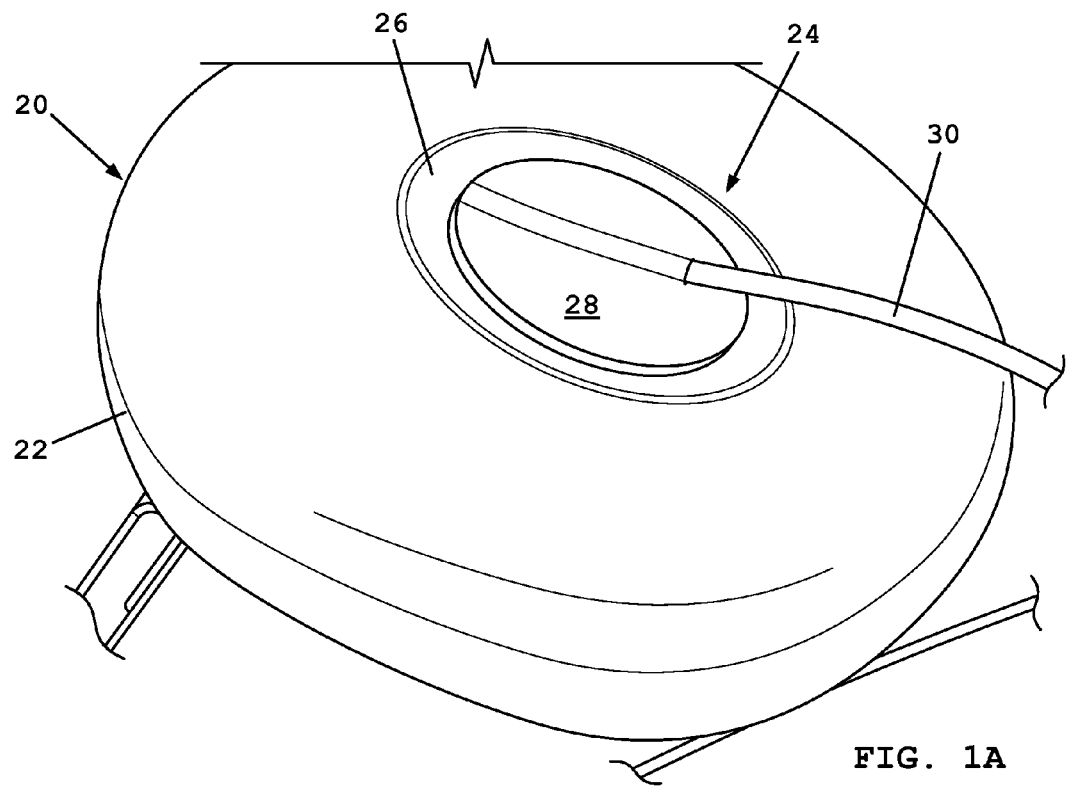
FIG. 1A shows a perspective view of an expandable implant having a valve assembly and a filling tube inserted into the valve assembly, in accordance with one embodiment of the present invention.
Figure 1B:
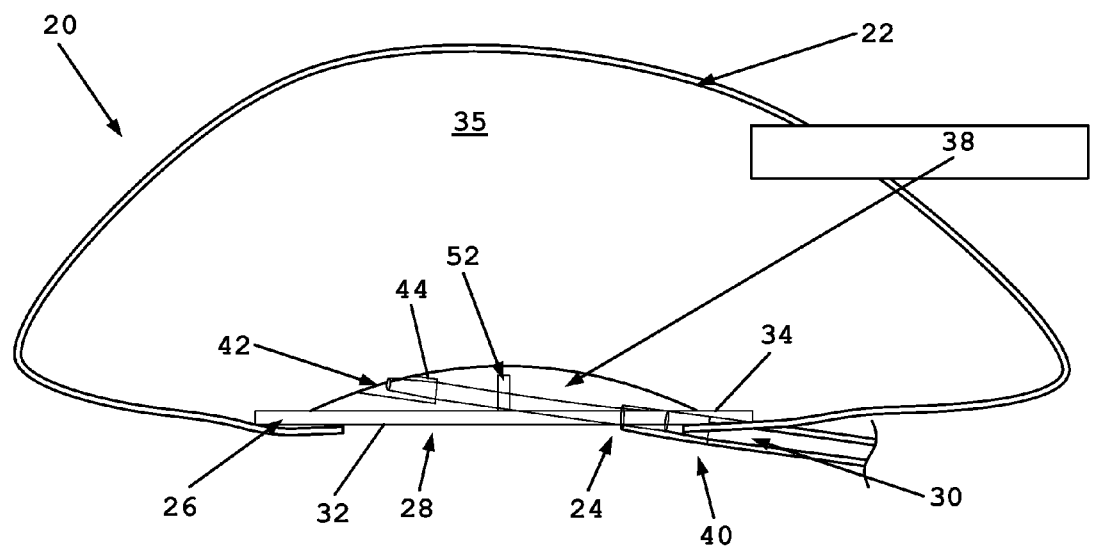
FIG. 1B shows a cross-sectional view of the expandable implant, the valve assembly, and the filling tube shown in FIG. 1A.

Referring to FIGS. 1A and 1B, in one embodiment, an expandable implant 20, such as a breast implant or tissue expander, preferably includes an outer shell 22 made of a flexible, biocompatible material such as silicone. The outer shell 22 is adapted to be filled with a solution, such as a saline solution, silicone gel, foam, or combinations thereof. The outer shell 22 desirably has an opening 24 that is closed by a biocompatible patch 26 of a valve assembly 28. In one embodiment, the valve assembly 28 is adapted to receive a filling tube 30 that enables the biocompatible solution to be added to or withdrawn from the outer shell 22 for adjusting the size of the expandable implant 20.

Figure 2:
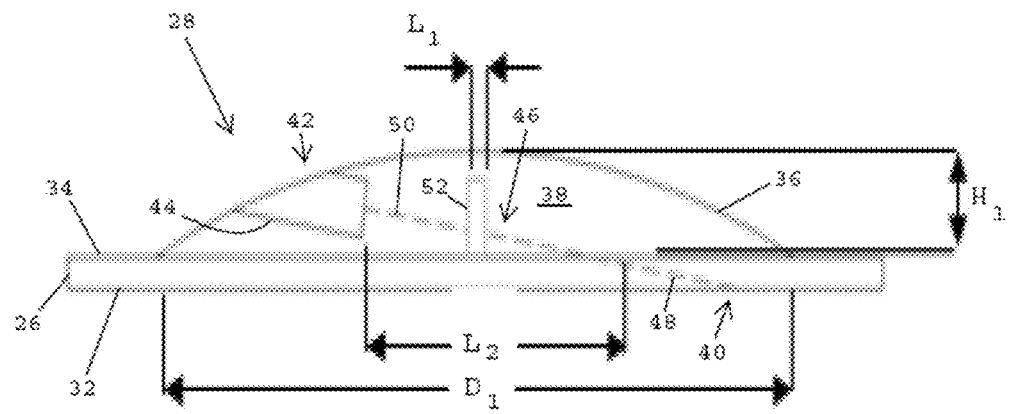
FIG. 2 shows a cross-sectional view of a valve assembly for an expandable implant, in accordance with one embodiment of the present invention.

Referring to FIGS. 1B and 2, in one embodiment, the valve assembly 28 desirably includes the biocompatible patch 26 that is secured to the opening 24 of the outer shell 22 of the expandable implant 20 (FIG. 1B) to close and seal the opening in the outer shell. The patch 26 desirably includes an outer face 32 that defines an outer surface of an expandable implant, and an inner face 34 that faces toward an interior chamber 35 of the outer shell 22 of the expandable implant 20.

The valve assembly 28 desirably includes a flexible, biocompatible layer that forms an inner shell 36 adapted to receive a material 38 having self-sealing properties such as liquid silicone rubber. As will be described in more detail below, when the filling tube 30 is withdrawn from the valve assembly 28, the self-sealing material 38 closes and seals the opening formed in the self-sealing material to seal the valve assembly 28.

In one embodiment, the valve assembly 28 preferably includes an inlet 40 accessible outside the expandable implant, which is adapted to receive the filling tube 30, and an outlet 42 adapted to receive and seat a distal end of the filling tube 30. In one embodiment, the outlet 42 includes a tubular shaped receiving chamber 44 that is located at a distal end of a filling tube insertion path. The receiving chamber 44 preferably maintains the shape and configuration of the outlet opening 42 in the wall of the inner shell 36.

Referring to FIG. 2, in one embodiment, the valve assembly 28 preferably includes a filling tube insertion pathway 46 having a proximal section 48 and a distal section 50. The valve assembly 28 includes a gap 52 (FIG. 1B) that is desirably formed in the middle of the filling tube insertion pathway 46. The gap 52 divides the filling tube insertion pathway 46 into the proximal section 48 and the distal section 50. After a solution has been added to or withdrawn from the implant, the filling tube is withdrawn from the valve assembly 28. As the filling tube is withdrawn, if the self-sealing material 38 located at the distal section 50 of the insertion pathway is unable to form a water-tight seal before the solution from inside the implant reaches the gap 52, the solution that escapes from the distal section 50 of the pathway will not advance into the proximal section 48 of the pathway, but will first be diverted into the gap 52. The diversion of the solution into the gap 52 will provide more time for the self-sealing material 38 within the proximal section 48 to close and form a water-tight seal. Although the present invention is not limited by any particular theory of operation, it is believed that providing at least one gap 52 along the length of the insertion pathway 46 enhances sealing of the valve assembly and desirably enables the overall length of the insertion pathway to be shorter than would otherwise be required. The proximal section 48 provides a backup for the distal section 50. If the distal section 50 is not fully sealed by the time the solution reaches the gap 52, the proximal section 48 seals to prevent leakage, as well.

Although the FIG. 2 embodiment shows only one gap 52, in other embodiments, more than one gap may be formed in the self-sealing material 38 along the insertion pathway 46. In one embodiment, the specific volume of the gap 52 may be modified to compliment the specific properties of the self-sealing material 38 that is used. In one embodiment, if the self-sealing material 38 is able to quickly self-seal, then the gap can have a smaller volume, but if the self-sealing material 38 is relatively slow to self-seal, then the gap should have more volume.

In one embodiment, the gap 52 formed in the self-sealing material 38 has a length $L_1$ of about 1 mm. In one embodiment, the gap 52 may be formed by making a knife cut in the self-sealing material 38 along the insertion path 46 of the filling tube. In one embodiment, the gap is formed by using a rib in a mold when casting the patch 26. The gap may also be formed by cross-linking the silicone rubber to define the metes and bounds of the gap.

In one embodiment, the insertion path 46 for the filling tube has a length $L_2$ of about 5-30 mm and more preferably about 20 mm. In one embodiment, the insertion path 46 has a length of at least 8 mm. In one embodiment, the inner shell 36 that contains the self-sealing material 38 has a diameter $D_1$ about 10-40 mm and more preferably about 38 mm. In one embodiment, the inner shell 36 has a diameter of at least 14 mm. In one embodiment, the inner shell 36 has a height $H_1$ of about 2-5 mm and more preferably about 4 mm. In one embodiment the inner shell 36 has a height $H_1$ of at least 3 mm.

The valve assembly 28 preferably includes the biocompatible patch 26 having the outer surface 32 and the inner surface 34. The inner shell 36 is secured over the inner surface 34 and is filled with the self-sealing material 38. In one embodiment, the filling tube insertion pathway 46 preferably extends diagonally through the self-sealing material 38 within the valve assembly 28. The inlet 40 and the outlet 42 are preferably aligned with one another so that the filling tube insertion path 46 defines a straight line extending from the inlet 40 and the outlet 42.

Figure 3:
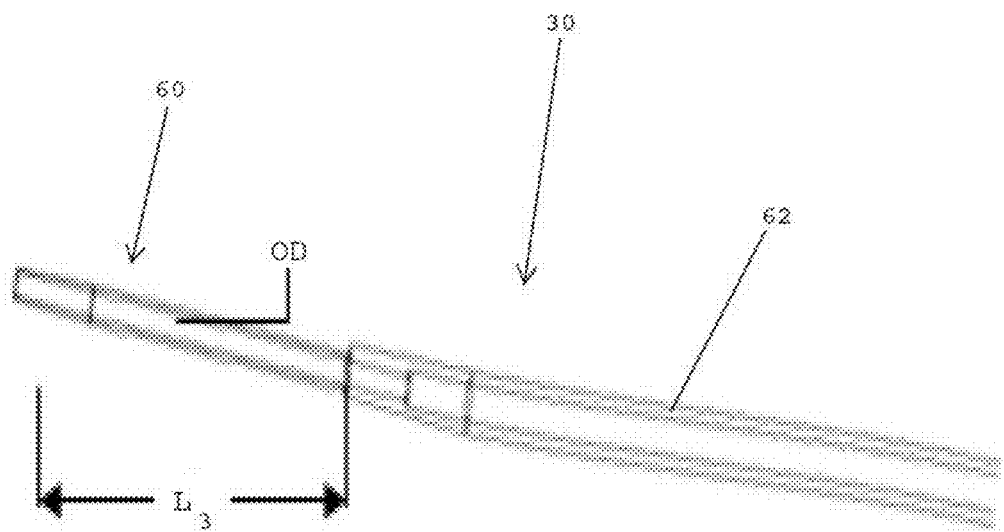
FIG. 3 shows a cross-sectional view of a filling tube for the valve assembly of FIG. 2, in accordance with one embodiment of the present invention.

Referring to FIGS. 2 and 3, in one embodiment, the filling tube 30 desirably has a distal end 60 having a tubular shape that is adapted to be inserted into the inlet 40 and advanced along the filling tube insertion pathway 46 until the distal end 60 of the filling tube is seated within the outlet chamber 44 at the outlet 42 of the valve assembly 28. As the distal end 60 of the filling tube 30 is advanced through the valve assembly, the distal end 60 forms an opening in the self-sealing material 38 located within the inner shell 36 of the valve assembly 28. The distal end 60 of the filling tube 30 is preferably made of a sturdy, biocompatible material such as stainless steel or plastic. The distal-most end is preferably blunt. In one embodiment, the filling tube 30 may include a flexible outer shaft 62 that extends proximally from the distal end 60 thereof. In one embodiment, the flexible outer shaft portion of the filling tube is preferably more flexible and less rigid than the distal end 60. In one embodiment, the distal end 60 has a length $L_3$ that is greater than the length $L_2$ of the insertion pathway 46. In one embodiment, the length $L_3$ of the distal end 60 of the filling tube 30 is about 3 mm greater than the length $L_2$ of the insertion pathway. In one embodiment, the length $L_3$ of the distal end 60 is about 20-30 mm and more preferably about 25 mm in length.

In one embodiment, the distal end 60 has an outer diameter OD of about 0.8-1.6 mm and more preferably about 1.2 mm. Although dimensions have been provided for the various components of the valve assembly and the filling tube, the dimensions disclosed herein may be modified depending upon the size of the implant and the size of the filling tube.

Figure 4:
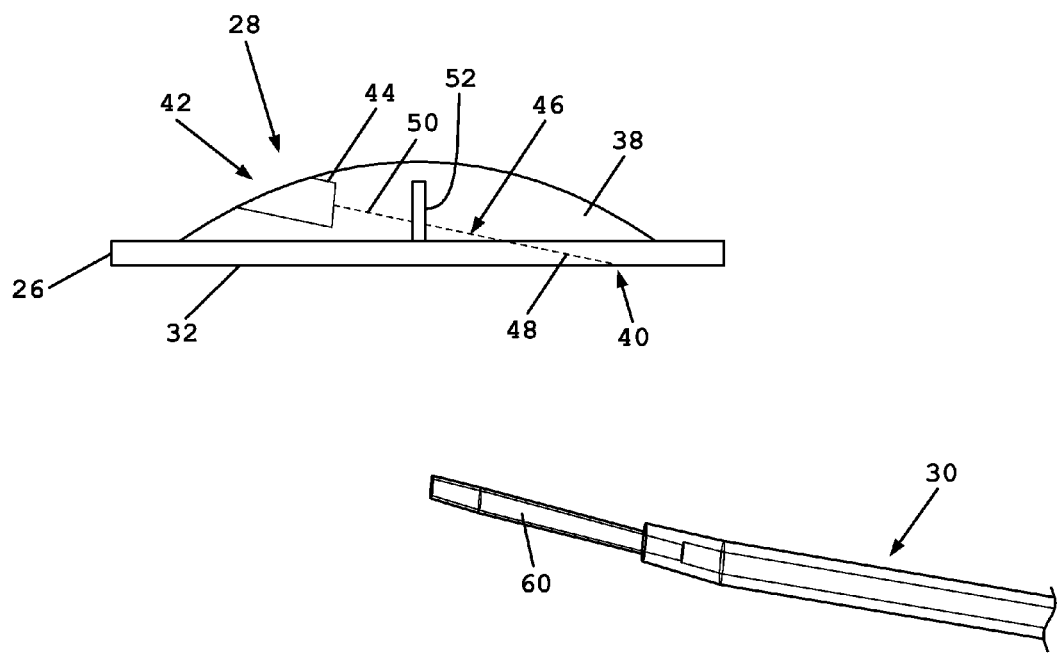
FIG. 4 shows the filling tube of FIG. 3 prior to insertion of the filling tube into the valve assembly of FIG. 2, in accordance with one embodiment of the present invention.

Referring to FIG. 4, in one embodiment, the volume of an expandable implant 20 (FIGS. 1A and 1B) may be adjusted by inserting the filling tube 30 into the valve assembly 28. In one embodiment, the distal end 60 is preferably juxtaposed with the inlet 40 accessible at the outer surface 32 of a biocompatible patch 26 so that the distal end 60 may be advanced through the self-sealing material 38 for being coupled with the outlet chamber 44 at the outlet 42 of the inner shell 36. As the distal end of the filling tube advances through the self-sealing material, the filling tube opens a pathway through the self-sealing material 38. After the filling tube is removed, the pathway formed in the self-sealing material 38 closes due to the very high elastic properties of the silicone rubber, which provides the material with self-sealing or self-healing properties.

Figure 5A:
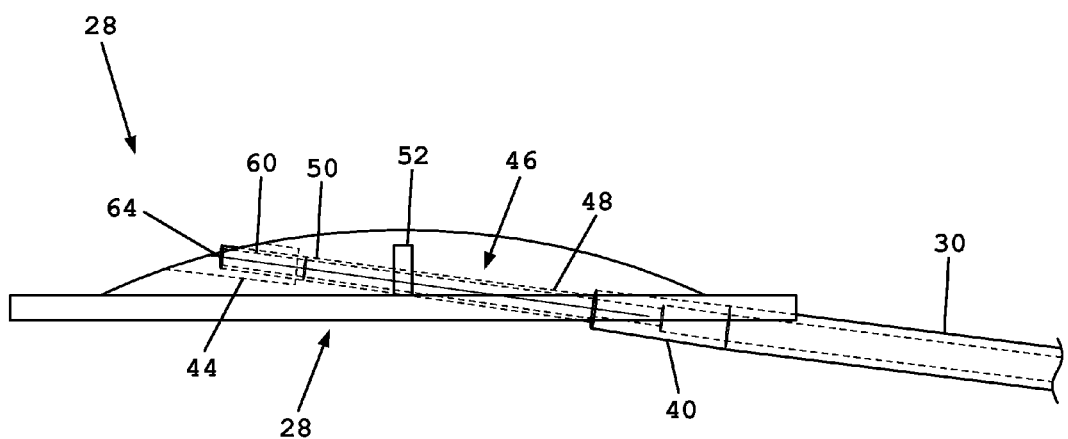
FIG. 5A shows the filling tube of FIG. 3 inserted into the valve assembly of FIG. 2, in accordance with one embodiment of the present invention.
Figure 5B:
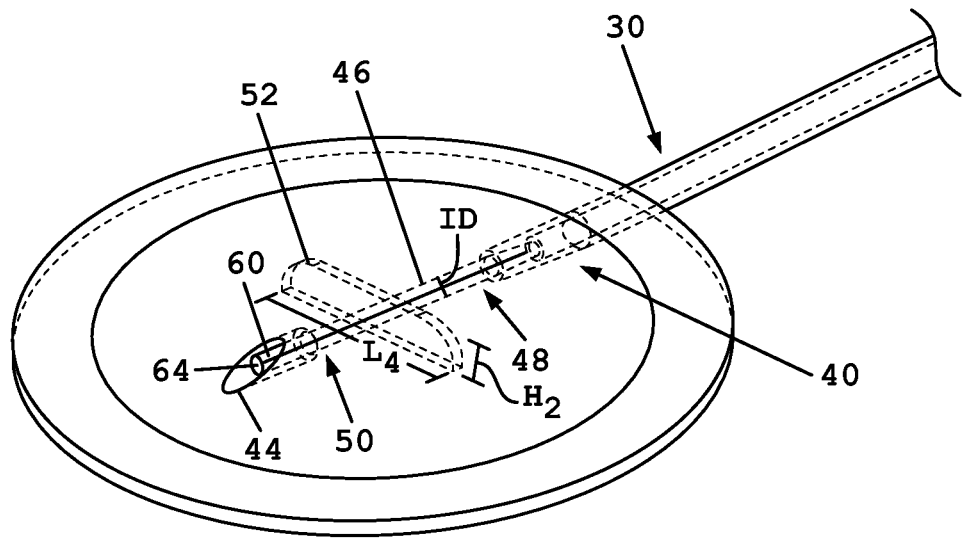
FIG. 5B shows a perspective view of the valve assembly and filling tube of FIG. 5A.
Figure 5C:
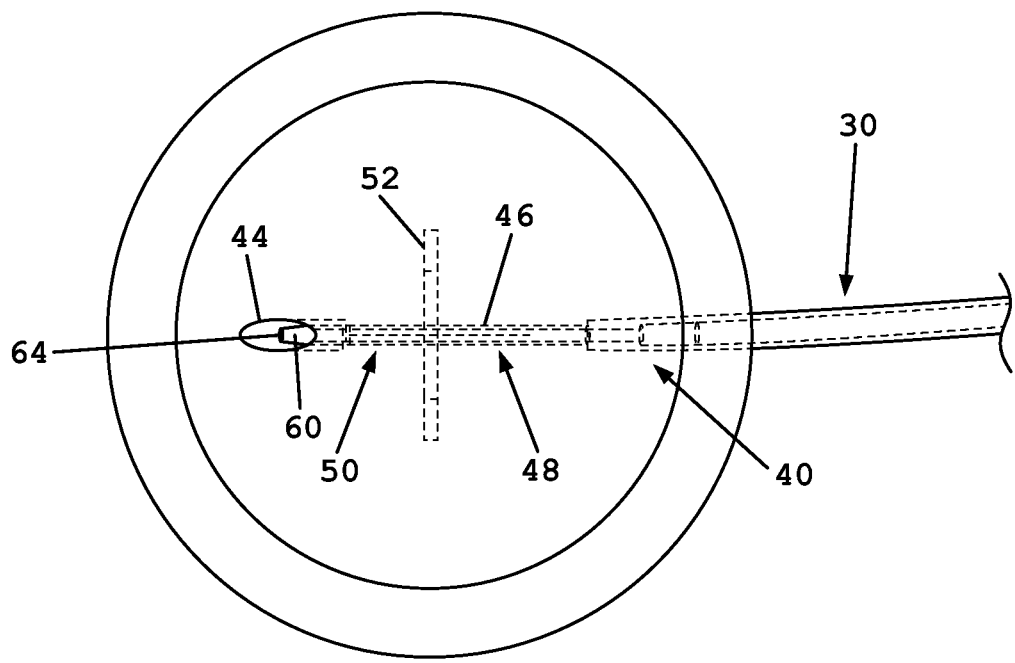
FIG. 5C shows a top plan view of the valve assembly and filling tube of FIG. 5A.

FIGS. 5A-5C show the filling tube 30 coupled with the valve assembly 28. In one embodiment, the distal end 60 of the filling tube 30 is coupled with the outlet chamber 44 so that an opening 64 at the distal end of the filling tube 30 is in communication with the internal chamber 35 within the outer shell 22 of the expandable implant 20 (FIG. 1B). The distal end 60 of the filling tube 30 extends along the filling tube insertion pathway 46 extending between the inlet 40 and the outlet chamber 44. The distal end 60 passes through the gap 52 formed in the self-sealing material 38, whereby the gap 52 divides the insertion pathway 46 into the proximal section 48 and the distal section 50.

Referring to FIG. 5B, in one embodiment, the gap 52 has a length $L_4$ of about 8-20 mm and a height $H_2$ of about 3-5 mm that covers a cross-sectional area ($L_4 \times H_2$) that is greater than the cross-sectional area ($3.14 \times r^2$) of the insertion pathway (ID=0.8-1.6 mm). In one embodiment, the gap 52 has a cross-sectional area of about 24-100 mm$^2$ and the insertion pathway has a cross-sectional area of about 0.5-2.0 mm$^2$ and more preferably about 1.15 mm$^2$. In one embodiment, the gap 52 has a volume (Length 8-20 mm, Height 3-5 mm, Width 1-3 mm) of about 24 mm$^3$-300 mm$^3$. The volume of the gap 52 may be modified as necessary to enhance the performance of the valve assembly.

A biocompatible solution, such as saline solution, may be introduced through the filling tube 30 and into the outer shell 22 of the expandable implant 20 (FIGS. 1A and 1B) for adjusting the internal volume of the expandable implant. Alternatively, the solution inside the outer shell of the implant 20 may be withdrawn through the filling tube 30 for reducing the size of the expandable implant 20.

Referring to FIG. 4, when the implant has been adjusted to a desired size by adding or withdrawing solution, the distal end 60 of the filling tube 30 may be withdrawn from the valve assembly 28. As the distal end 60 is withdrawn, the self-sealing material 38 fills the void left by the retracted distal end of the filling tube for sealing the void so as to prevent the solution from leaking from the inlet 40 of the inner shell 36 of the valve assembly. During withdrawal of the distal end 60 of the filling tube, the distal end 60 is first retracted from the distal section 50 of the insertion pathway 46, whereupon the self-sealing material 38 in the distal section 50 collapses into the void left by the retracted distal end 60. The self-sealing material in the proximal section 48 collapses into the void as the distal end 60 of the filling tube is retracted from the proximal section 48 of the insertion pathway 46. If the solution from the internal chamber 35 (FIG. 1B) of the implant reaches the gap 52 before the proximal section 48 has closed to form a water-tight seal, the solution is first diverted into the gap 52 to direct the flow of the solution away from the proximal section 48. The gap 52 provides a flow diversion that provides sufficient time for the self-sealing material in the proximal section 48 to form a water-tight seal so that the solution cannot escape from the inlet 40 of the valve assembly 28.

Figure 6A:
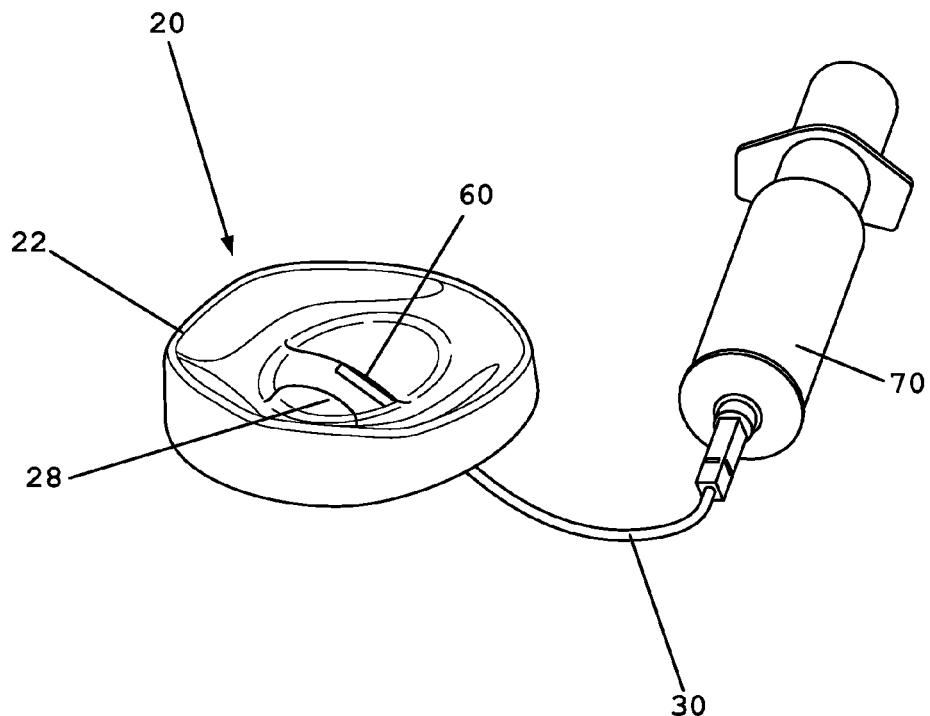
FIGS. 6A and 6B show a method of testing an expandable implant having a valve assembly, in accordance with one embodiment of the present invention.
Figure 6B:
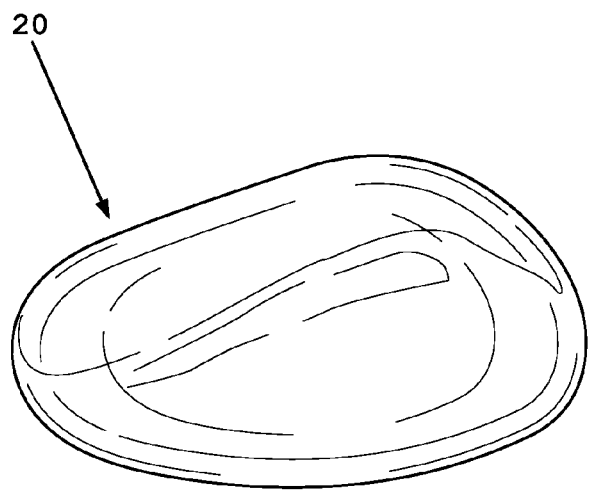

Referring to FIGS. 6A and 6B, in one embodiment, a leak test may be performed on an expandable implant 20 having a valve assembly 28 that closes a mandrel opening of an outer shell 22. Referring to FIG. 6A, in one embodiment, the filling tube 30 is coupled with the valve assembly 28 so that the opening at the distal end 60 of the filling tube 30 is in fluid communication with the internal chamber 35 (FIG. 1B) inside the outer shell 22 of the expandable implant 20. A syringe 70 is connected with a proximal end of the filling tube 30 to fill the outer shell 22 of the expandable implant 20 with air. The filling tube 30 is removed from the valve assembly 28 and the self-sealing material seals the valve assembly. The expanded implant 20 is preferably submerged in water and squeezed while under the water. If air bubbles are evident when the expandable implant 20 is squeezed, then the valve assembly 28 is defective and the product is rejected. If no air bubbles are visible during the squeeze test, the valve assembly is fully operational and the product is accepted.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A valve assembly for an expandable implant, said valve assembly comprising:
   an inner shell having an inlet and an outlet;
   a self-sealing material disposed within said inner shell, wherein said self-sealing material is a liquid silicone material;
   an insertion pathway extending through said liquid silicone material, wherein said insertion pathway extends from said inlet to said outlet of said inner shell;
   at least one gap formed in said liquid silicone material and intersecting said insertion pathway to divide said insertion pathway into a proximal section and a distal section, wherein said at least one gap spaces said proximal and distal sections of said insertion pathway from one another.

2. The valve assembly as claimed in claim 1, wherein said outlet of said inner shell comprises an outlet opening passing through said inner shell.

3. The valve assembly as claimed in claim 2, wherein said outlet opening has a cylindrical or circular shape.

4. The valve assembly as claimed in claim 1, wherein said insertion pathway extends along a straight line between said inlet and said outlet of said inner shell.

5. The valve assembly as claimed in claim 4, wherein said insertion pathway extends diagonally through said self-sealing material disposed within said inner shell.

6. The valve assembly as claimed in claim 1, wherein said expandable implant comprises an outer shell having an outer surface, an inner surface, and an outer shell opening extending from the outer surface to the inner surface of said outer shell, wherein said valve assembly covers said outer shell opening so that said inner shell is disposed inside said outer shell.

7. The valve assembly as claimed in claim 6, further comprising a filling tube passing through said inlet of said inner shell of said valve assembly and having a distal end coupled with said outlet of said inner shell for being in fluid communication with an internal chamber of said outer shell of said implant.

8. The valve assembly as claimed in claim 7, wherein said outer shell of said implant contains a solution having less viscosity than said liquid silicone material disposed within said inner shell of said valve assembly.

9. The valve assembly as claimed in claim 7, wherein said self-sealing material comprises a liquid silicone rubber and said solution within said outer shell of said implant is selected from the group consisting of saline solution, silicone gel, foam, and combinations thereof.

10. The valve assembly as claimed in claim 1, wherein said valve assembly further comprises a biocompatible patch and said inner shell is secured to said biocompatible patch, and wherein said expandable implant has an outer shell with an outer shell opening and said patch closes said outer shell opening for sealing said expandable implant.

11. The valve assembly as claimed in claim 1, wherein said at least one gap in said liquid silicone material has a larger cross-sectional area than a cross-sectional area defined by said insertion pathway.

12. The valve assembly as claimed in claim 11, wherein said gap has a cross-sectional area of 24-100 $mm^2$ and said insertion pathway has a cross-sectional area of 0.5-2.0 $mm^2$.

13. An expandable implant comprising:
   an outer shell having an outer surface, an inner surface, and an outer shell opening extending from the outer surface to the inner surface;
   a valve assembly closing said outer shell opening, said valve assembly comprising
      an inner shell having an inlet and an outlet,
      a self-sealing material disposed within said inner shell, wherein said self-sealing material is a liquid silicone rubber,
      an insertion pathway extending through said liquid silicone rubber, wherein said insertion pathway extends from said inlet to said outlet of said inner shell, and
      at least one gap formed in said liquid silicone rubber and intersecting said insertion pathway extending through said liquid silicone rubber to define a proximal section of said insertion pathway and a distal section of said insertion pathway, wherein said at least one gap formed in said liquid silicone rubber spaces and divides said proximal and distal sections of said insertion pathway from one another.

14. The expandable implant as claimed in claim 13, further comprising a filling tube extending through said valve assembly for opening said valve assembly for selectively inflating and deflating said implant using a solution.

15. The implant as claimed in claim 14, wherein said filling tube, extending through said valve assembly, passes through said inlet of said inner shell, extends along said insertion pathway through said liquid silicone rubber, and is in communication with said outlet of said inner shell.

16. The implant as claimed in claim 13, wherein said outlet of said inner shell comprises an outlet opening passing through said inner shell and being in communication with an internal chamber of said outer shell of said expandable implant.

17. The implant as claimed in claim 16, wherein said outlet opening has a cylindrical or circular shape.

18. The implant as claimed in claim 13, wherein said insertion pathway extends along a straight line between said inlet and said outlet of said inner shell.

19. The implant as claimed in claim 18, wherein said insertion pathway extends diagonally through said liquid silicone rubber disposed within said inner shell.

20. The implant as claimed in claim 13, further comprising:
   a filling tube having a distal end insertable into said inlet of said inner shell of said valve assembly and advanceable to said outlet of said inner shell for filling said outer shell of said expandable implant with a solution that has less viscosity than said liquid silicone rubber.

21. The implant as claimed in claim 19, wherein said self-sealing material comprises a liquid silicone gel, and wherein said solution within said expandable implant is selected from the group consisting of saline solution, silicone gel, foam, and combinations thereof.

22. The implant as claimed in claim 13, wherein said valve assembly further comprises:
   a biocompatible patch having an outer surface and an inner surface;
   said inner shell being secured to said inner surface of said patch;
   said patch closing said outer shell opening, wherein said inner shell is disposed inside said outer shell.

* * * * *